(12) United States Patent
Schotes et al.

(10) Patent No.: US 10,252,990 B2
(45) Date of Patent: Apr. 9, 2019

(54) PROCESS FOR THE PREPARATION OF 2-ALKYL-4-TRIFLUOROMETHYL-3-ALKYLSULPHONYLBENZOIC ACIDS BY CHEMOSELECTIVE THIOETHER OXIDATION

(71) Applicant: Bayer CropScience Aktiengesellschaft, Monheim am Rhein (DE)

(72) Inventors: Christoph Schotes, Düsseldorf (DE); Christoph Sämann, Düsseldorf (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/778,699

(22) PCT Filed: Nov. 28, 2016

(86) PCT No.: PCT/EP2016/078971
§ 371 (c)(1),
(2) Date: May 24, 2018

(87) PCT Pub. No.: WO2017/093172
PCT Pub. Date: Jun. 8, 2017

(65) Prior Publication Data
US 2018/0354898 A1    Dec. 13, 2018

(30) Foreign Application Priority Data

Nov. 30, 2015    (EP) .................................... 15196992

(51) Int. Cl.
| | | |
|---|---|---|
| *C07C 315/02* | (2006.01) | |
| *C07C 319/14* | (2006.01) | |
| *C07C 323/62* | (2006.01) | |
| *C07C 323/65* | (2006.01) | |
| *C07C 317/44* | (2006.01) | |
| *C07C 323/09* | (2006.01) | |

(52) U.S. Cl.
CPC .......... *C07C 315/02* (2013.01); *C07C 317/44* (2013.01); *C07C 319/14* (2013.01); *C07C 323/09* (2013.01); *C07C 323/62* (2013.01); *C07C 323/65* (2013.01)

(58) Field of Classification Search
CPC ... C07C 315/02; C07C 319/14; C07C 323/62; C07C 323/65; C07C 317/44; C07C 323/09
See application file for complete search history.

(56) References Cited

U.S. PATENT DOCUMENTS 7,932,211 B2 *  4/2011  Ahrens .................. A01N 43/56
                                                    504/282

FOREIGN PATENT DOCUMENTS

| WO | 2008125214 A1 | 10/2008 |
| WO | 2012126932 A1 | 9/2012 |

OTHER PUBLICATIONS

International Search Report of International Patent Application No. PCT/EP2016/078971 dated Mar. 17, 2017.

* cited by examiner

*Primary Examiner* — Rosalynd A Keys
(74) *Attorney, Agent, or Firm* — McBee Moore Woodward & Vanik IP, LLC

(57) ABSTRACT

A process for the preparation of 2-alkyl-4-trifluoromethyl-3-alkylsulfonylbenzoic acids of the formula (I) is described.

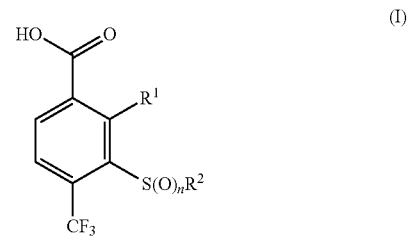

Herein, the substituents are radicals such as alkyl and substituted phenyl.

15 Claims, No Drawings

PROCESS FOR THE PREPARATION OF 2-ALKYL-4-TRIFLUOROMETHYL-3-ALKYLSULPHONYLBENZOIC ACIDS BY CHEMOSELECTIVE THIOETHER OXIDATION

CROSS REFERENCE TO RELATED APPLICATIONS

This application is a National Stage entry of International Application No. PCT/EP2016/078971 filed 28 Nov. 2016, which claims priority to European Patent Application No. 15196992.0, filed 30 Nov. 2015.

BACKGROUND

Field

The invention relates to a process for the preparation of 2-alkyl-4-trifluoromethyl-3-alkylsulfonylbenzoic acids which are of use as intermediates for the preparation of agrochemically effective substances.

A number of publications disclose agrochemically effective substances for whose preparation 2-alkyl-4-trifluoromethyl-3-alkylsulfonylbenzoic acids are required. Thus, WO 2008/125214 A1 discloses herbicidally effective 4-(4-trifluoromethyl-3-thiobenzoyl)pyrazoles. WO 2012/126932 A1 discloses herbicidally effective N-(1,3,4-oxadiazol-2-yl)arylcarboxamides, including those with a similar substitution pattern in the phenyl ring to the compounds disclosed in WO 2008/125214 A1.

WO 2008/125214 A1 also discloses a process for the preparation of 2-methyl-4-trifluoromethyl-3-methylsulfonylbenzoic acid. In this process, 3-fluoro-2-methyl-4-trifluoromethylbenzoic acid is reacted with sodium hydride and sodium thiomethylate to give the 2-methyl-3-methylthio-4-trifluoromethylbenzoic acid, which is then oxidized to the 2-methyl-3-methylsulfonyl-4-trifluoromethylbenzoic acid.

Disadvantages of this process are the use of the difficult-to-prepare 3-fluoro-2-methyl-4-trifluoromethylbenzoic acid, as well as the introduction of the methyl group by metallation of the 3-fluoro-2-methyl-4-trifluoromethylbenzoic acid with at least 2 mol equivalents of butyllithium at low temperature, followed by a reaction with the toxic methyl iodide. This process is complex and, on account of the only low yield upon introducing the methyl group (50.7% of theory), moreover, uneconomical.

Processes for preparing substituted benzoic acids by transition-metal-catalysed cyanations of chloroaromatics and subsequent saponification of the cyano group to the acid group are likewise known. It is disadvantageous here that highly toxic cyanides as well as expensive and chemically sensitive catalysts are used. Complex processing of the waste streams must also take place here in order to exclude damage for people and environment.

It is furthermore known that sulfoxide groups can be exchanged for metal with the help of organometallic compounds such as lithiumalkyl or lithiumaryls, and the resulting species can then be reacted with carbon dioxide to give a carboxylic acid. However, in this type of reaction, undesired reactions arise depending on the type of substituents.

SUMMARY

The object of the present invention is to provide a process for preparing 2-alkyl-4-trifluoromethyl-3-alkylsulfonylbenzoic acids which overcomes the disadvantages of the processes known from the prior art.

It has now been found that 2-alkyl-4-trifluoromethyl-3-alkylsulfonylbenzoic acids can be prepared starting from 1,3-dichloro-2-alkyl-4-trifluoromethylbenzenes without using cyanides or transition metal catalysts by means of the reaction sequence of a double thiolation, selective oxidation of a thioether group, exchange of the sulfoxide group for a metal, carboxylation and oxidation of the remaining thioether group.

The present invention therefore provides a process for the preparation of 2-alkyl-4-trifluoromethyl-3-alkylsulfonylbenzoic acids of the general formula (I), characterized in that a) in a first step a 1,3-dichloro-2-alkyl-4-trifluoromethylbenzene (II) is reacted with a thiolate (IV) to give an aryl bisthioether (III), b) in a second step the aryl bisthioether (III) is reacted with an oxidizing agent selectively to give an aryl monosulfoxide monothioether (V), c) in a third step an exchange of the sulfoxide group for a metal takes place and the organometallic compound thus obtained is converted to the benzoic acid (VII), and d) in a fourth step the remaining thio group is oxidized with an oxidizing agent, optionally in the present of an oxidation catalyst:

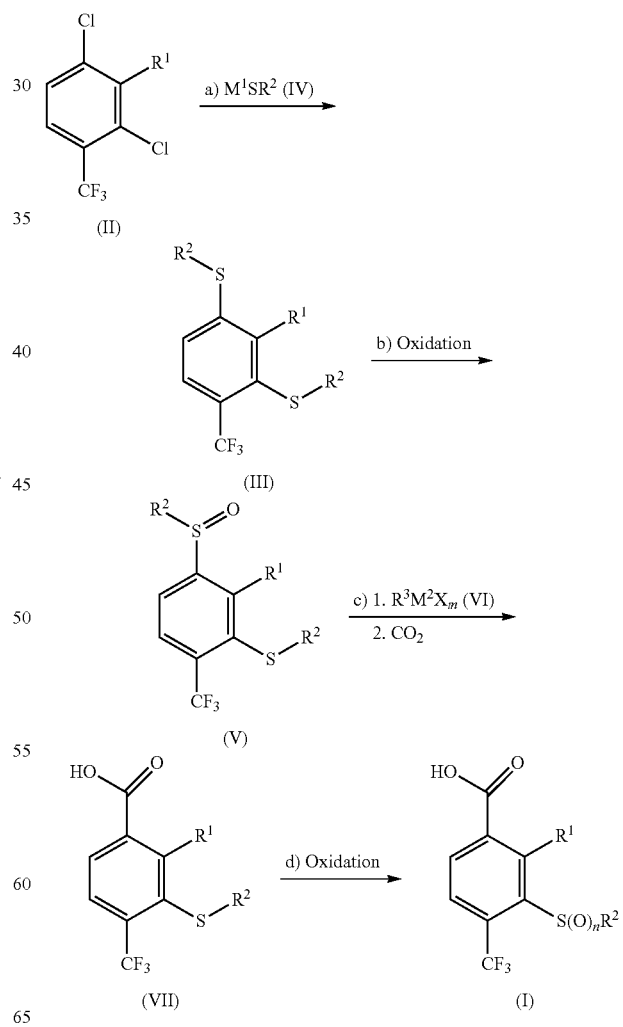

and e) in which the substituents are defined as follows:
$R^1$ and $R^2$ are, independently of one another, $C_1$-$C_4$-alkyl or phenyl substituted by s radicals from the group consisting of chlorine, fluorine, methoxy and ethoxy,
$R^3$ is $C_1$-$C_{10}$ alkyl or phenyl substituted by s radicals from the group consisting of chlorine, fluorine, methoxy and ethoxy,
$M^1$ is lithium, sodium or potassium,
$M^2$ is magnesium, lithium or zinc,
X is chloride, bromide or iodide,
m is 0 or 1,
n is 1 or 2,
s is 0, 1, 2 or 3.

DETAILED DESCRIPTION OF A PREFERRED EMBODIMENT

Essential advantages of the process according to the invention are:
the good differentiation of the two chlorine substituents on compound (II) without use of a transition metal catalyst,
the selective thioetheroxidation with favourable reagents such as peracetic acid or $H_2O_2$,
the generation of the carboxylic acid group with the help of a simple organometallic reagent in conjunction with favourable and easy-to-handle carbon dioxide.

In the formulae (I), (II), (III), (IV), (V), (VI) and (VII). alky radicals with more than two carbon atoms can be straight-chain or branched. Alkyl radicals are e.g. methyl, ethyl, n- or isopropyl, n-, iso-, t- or 2-butyl.

Sodium thiomethylate (NaSMe) and potassium thiomethylate (KSMe) are particularly well suited as thiolate (IV).

In the first step of the process according to the invention, the compound of the general formula (IV) is used in a quantitative ratio of 2:1 to 4:1 mol equivalents, based on the compound of the general formula (II). Preference is given to a quantitative ratio of 2:1 to 3:1, particularly preferably 2.5:1.

The compounds of the general formula (IV) can be prepared either in-situ or ex-situ from the corresponding thiols and a base, such as alkali metal hydroxides, alkaline earth metal hydroxides, alkali metal carbonates, alkali metal acetates, alkali metal alcoholates and organic bases. Suitable bases are LiOH, NaOH, KOH, Ca(OH)$_2$, Na$_2$CO$_3$, K$_2$CO$_3$, Cs$_2$CO$_3$, NaOAc, KOAc, LiOAc, NaOMe, NaOEt, NaO-t-Bu, KO-t-Bu, trialkylamines, alkylpyrridines, phosphazenes and 1,8-diazabicyclo[5.4.0]undecene.

The reaction of the first step of the process according to the invention is generally carried out in a solvent such as acetonitrile, dimethylformamide, dimethylacetamide, dimethyl sulfoxide or N-methyl-2-pyrrolidone. Preference is given to dimethyl sulfoxide, dimethylacetamide, dimethylformamide and N-methyl-2-pyrrolidone, particularly preferably dimethyl sulfoxide.

The reaction in the first step of the process according to the invention is generally carried out at a temperature from 0 to 100° C., preferably 20 to 70° C., particularly preferably 30 to 40° C. The reaction can also be carried out under increased or reduced pressure.

Excesses of the compound (IV) may result in a partial demethylation of the compound (III). This can be compensated by topping up alkylating agents such as Me$_2$SO$_4$, MeI, MeBr, MeCl or dimethyl carbonate. Preference is given to Me$_2$SO$_4$.

In the second step of the process according to the invention, the oxidizing agent is used in the quantitative ratio of 2:1 to 4:1 mol equivalents, based on the compound of the general formula (III). Preference is given to 1.5:1 to 3.5:1, particularly preferably 3:1. Suitable oxidizing agents are $H_2O_2$, peracetic acid or meta-chloroperbenzoic acid. Preference is given to $H_2O_2$. Surprisingly here, the thioether group in the para position relative to the trifluoromethyl group is selectively oxidized to the sulfoxide.

The reaction of the second step of the process according to the invention is generally carried out in a solvent such as acetonitrile, ethyl acetate, butyl acetate, toluene, chlorobenzene, dichloromethane, acetic acid or propionic acid. Preference is given to dichloromethane, acetic acid and propionic acid, particularly preferably acetic acid and propionic acid.

In the reaction in the second step of the process according to the invention, it is also possible to use oxidation catalysts based on vanadium or iron that are known to the person skilled in the art.

The reaction in the second step of the process according to the invention is generally carried out at a temperature from 0 to 50° C., preferably at 10 to 30° C. and particularly preferably at 20° C. The reaction can also be carried out under increased or reduced pressure.

In the third step of the process according to the invention, the sulfoxide group in compounds of the type (V) is exchanged for a metal with the help of an organometallic compound. The organometallic reagents used are compounds of the general formula (VI) in which $M^2$ is magnesium, zinc or lithium, and $R^3$ is a radical from the group consisting of methyl, ethyl, isopropyl, butyl, isobutyl, tert-butyl, hexyl, phenyl, vinyl, allyl and mesityl. Preference is given to Grignard compounds in which $M^2$=Mg, X=Cl or Br and $R^3$ is a radical from the group consisting of isopropyl, butyl, hexyl or ethyl. Particular preference is given to isopropylmagnesium chloride, ethylmagnesium bromide and butylmagnesium chloride.

The organometallic reagents can also be used in combination with LiCl. The reagents are used as solutions in solvents such as tetrahydrofuran, 2-methyltetrahydrofuran, dioxane, diethyl ether, tert-butyl methyl ether, or cyclopentyl methyl ether. Mixtures of these solvents are also suitable. The organometallic reagents are used in a quantitative ratio of 2:1 to 0.7:1 mol equivalents, based on the compound of the general formula (V). Preference is given to 1:1 to 1.5:1, particularly preferably 1.1:1.

The compounds of the general formula (V) are generally dissolved in a solvent in the reaction in the third step of the process according to the invention. Suitable solvents are tetrahydrofuran, 2-methyltetrahydrofuran, dioxane, diethyl ether, tert-butyl methyl ether, toluene, xylene and cyclopentyl methyl ether. Preference is given to toluene, tetrahydrofuran and 2-methyltetrahydrofuran, particularly preferably toluene.

Following formation of the organometallic species, this is captured with an electrophile such as carbon dioxide, dimethyl carbonate or diethyl carbonate. Preference is given to carbon dioxide. The electrophiles are generally used in excess (1.1-20 mol equivalents).

The reaction in the third step of the process according to the invention is generally carried out at a temperature of −80 to 0° C., preferably −30 to −10° C., particularly preferably at −25° C. The reaction can also be carried out under increased or reduced pressure.

In the fourth step of the process according to the invention, the thio group of the compound (VII) is oxidized with hydrogen peroxide, optionally in the presence of an oxidation catalyst. Suitable oxidation catalysts are Na$_2$WO$_4$, Na$_2$MoO$_4$, and hydrates thereof, and also sulphuric acid in combination with an organic acid, such as acetic acid, formic acid or trifluoroacetic acid.

The oxidation catalysts are used in amounts of 1 to 20 mol %, based on the compound of the general formula (VII). Preference is given to 5 to 15 mol %, particularly preferably 10 mol %.

Hydrogen peroxide is used in an amount of 2 to 10, preferably 3 to 8, particularly preferably 3.5 to 5 mol equivalents, based on the compound of the general formula (VII). Usually, the hydrogen peroxide is used as 20-35% strength aqueous solution.

The reaction in the fourth step of the process according to the invention is generally carried out at a temperature of 30 to 110° C., preferably 40 to 80° C., particularly preferably 50 to 70° C. The reaction can also be carried out under increased or reduced pressure.

The reaction of the fourth step of the process according to the invention is generally carried out in a solvent. Suitable solvents are toluene, chlorobenzene, dichlorobenzene, ethyl acetate, butyl acetate, acetic acid, formic acid and water. Preference is given to toluene, ethyl acetate, butyl acetate, formic acid and water. Particular preference is given to toluene, butyl acetate, acetic acid and water.

Compounds of the formula (III) in which R$^1$ and R$^2$ are specific substituents are novel and are very highly suitable as starting material for the second step of the process according to the invention. The present invention therefore further provides compounds of the formula (III),

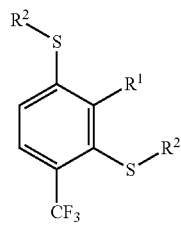
(III)

in which
R$^1$ and R$^2$ independently of one another are C$_1$-C$_4$-alkyl or phenyl substituted by s radicals from the group consisting of chlorine, fluorine, methoxy and ethoxy,
s is 1, 2 or 3.

Preferably, R$^1$ and R$^2$ in formula (III), independently of one another, are methyl, ethyl, n-propyl, isopropyl or n-butyl. Particularly preferably, R$^1$ and R$^2$ are in each case methyl.

Compounds of the formula (V) are likewise novel and are very highly suitable as starting material for the third step of the process according to the invention. The present invention therefore further provides compounds of the formula (V),

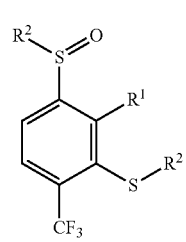
(V)

in which
R$^1$ and R$^2$ independently of one another are C$_1$-C$_4$-alkyl or phenyl substituted by s radicals from the group consisting of chlorine, fluorine, methoxy and ethoxy,
s is 1, 2 or 3.

Preferably, R$^1$ and R$^2$ in formula (V) are independently of one another methyl, ethyl, n-propyl, isopropyl or n-butyl. Particularly preferably, R$^1$ and R$^2$ are in each case methyl.

Using high excesses of the oxidizing agent, as well as relatively high temperatures and relatively long reaction times in step 2 of the process according to the invention gives compounds of the general formula (VIII). These are likewise novel and can serve as starting materials of other agrochemically effective compounds. The present invention therefore further provides compounds of the general formula (VIII),

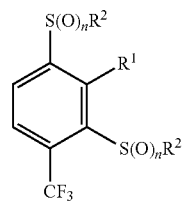
(VIII)

in which
R$^1$ and R$^2$ independently of one another are C$_1$-C$_4$-alkyl or phenyl substituted by s radicals from the group consisting of chlorine, fluorine, methoxy and ethoxy,
s is 1, 2 or 3
n is 1 or 2.

The examples below illustrate the invention in more detail without limiting it thereto.

Preparation of 2-methyl-3-(methylsulfonyl)-4-(trifluoromethyl)benzoic acid

Step 1: 2-methyl-1,3-bis(methylsulfanyl)-4-(trifluoromethyl)benzene 2,4-Dichloro-3-methyltrifluorobenzene (29.7 g, 130 mmol, 1 equiv) are initially introduced into 150 ml of DMSO and stirred for 10 min until a clear solution is formed NaSMe. (24 g, 325 mmol, 2.5 equiv) are added in portions with ice cooling. After the exothermy has subsided, the mixture is heated to 40° C. and after-stirred for 20 h. After cooling to room temperature, 3.3 g (26 mmol, 0.2 equiv) of Me$_2$SO$_4$ are added and the mixture is after-stirred for 30 min. With cooling, 30 ml of 20% strength NaOH are added and the mixture is after-stirred for 30 min. The mixture is diluted with 250 ml of water and extracted three times with methylcyclohexane. The combined organic phases are washed with water and saturated sodium chloride solution, dried over Na$_2$SO$_4$ and the solvent is removed under reduced pressure. 29.5 g of 2-methyl-1,3-bis(methylsulfanyl)-4-(trifluoromethyl)benzene (88% yield) are obtained as a colourless oil.

$^1$H NMR (600 MHz, CDCl$_3$) δ=7.53 (d, J=8.5 Hz, 1H), 7.14 (d, J=8.5 Hz, 1H), 2.65 (s, 3H), 2.50 (s, 3H), 2.26 (s, 3H). GC/MS: m/e=252 (M); 237 (M-H$_3$C.).

Step 2: 2-methyl-3-methylsulfanyl-1-methylsulfinyl-4-(trifluoromethyl)benzene

2-Methyl-1,3-bis(methylsulfanyl)-4-(trifluoromethyl) benzene (2 g, 7.9 mmol, 1 equiv) is initially introduced with 0.5 ml of acetic acid (8.7 mmol, 1.1 equiv). 2.05 ml of a 35% strength H$_2$O$_2$ solution (23.8 mmol, 3 equiv) are metered in over 1 hour and the mixture is after-stirred for 2 h at room temperature. The mixture is admixed with a bisulphite solution in order to destroy peroxides. The acetic acid is removed on a rotary evaporator. Water and dichloromethane are added and the organic phase is separated off. This is washed with water and bicarbonate solution, then the solvent is removed on a rotary evaporator. This gives 2-methyl-3-methylsulfanyl-1-methylsulfinyl-4-(trifluoromethyl)benzene as white solid in a yield of 75%. Any amounts of bis-sulfoxide present (general compound VIII where R$^1$=R$^2$=Me, n=1) can be separated off by recrystallization from MeOH/water or by chromatography.

$^1$H-NMR (600 MHz, CDCl$_3$): δ 8.10 (d, J=8.3 Hz, 1H) 7.85 (d, J=8.3 Hz, 1H), 2.71 (s, 3H), 2.64 (s, 3H), 2.29 (s, 3H). GC/MS: m/e=268.

Step 3: 2-methyl-3-methylsulfanyl-4-(trifluoromethyl)benzoic acid

All operations are carried out under protective gas. 60 ml of toluene are initially introduced and cooled to –25° C. 2-Methyl-3-methylsulfanyl-1-methylsulfinyl-4-(trifluoromethyl)benzene (10 g, 36.4 mmol, 1 equiv) is dissolved in 40 ml of toluene. In another vessel, 15 ml of a 3.26 molar EtMgBr/2-methyltetrahydrofuran solution are initially introduced and diluted with 24.3 ml of tetrahydrofuran and 9.3 ml of 2-methyltetrahydrofuran. The titer of the resulting Grignard solution is 1.03 M.

Now, the solutions of 2-methyl-3-methylsulfanyl-1-methylsulfinyl-4-(trifluoromethyl)benzene and EtMgBr are introduced dropwise in parallel into the reaction flask at –25° C. over 30 min. The mixture is after-stirred at this temperature for 40 min, then dry CO$_2$ is introduced. The internal temperature is kept below –10° C. The reaction solution is allowed to reach room temperature, and is then admixed with concentrated HCl. The phases are separated and the aqueous phase is after-washed twice with toluene. The combined organic phases are rendered basic with 1N aqueous NaOH. The aqueous phase is separated off and the organic phase is after-extracted twice with 1N NaOH. The aqueous phase is adjusted to pH 0-1 with concentrated HCl and extracted three times with ethyl acetate. The combined organic phases are dried over Na$_2$SO$_4$, then the solvents are removed under reduced pressure. 6.2 g of 2-methyl-3-methylsulfanyl-4-(trifluoromethyl)benzoic acid (59% yield according to NMR quantification) are isolated as a slightly yellowish solid.

Step 4: 2-Methyl-3-(methylsulfonyl)-4-(trifluoromethyl)benzoic acid 2-methyl-3-(methylsulfanyl)-4-(trifluoromethyl)benzoic acid (9.6 g, 38 mmol, 1 equiv) are dissolved in 60 ml of n-butyl acetate and 1.1 g (3.8 mmol, 0.1 equiv) of sodium tungstate dihydrate are added. The mixture is stirred intensively and heated to 55° C. By means of injection pump, 16.2 ml (190 mmol, 5 equiv) of 35% strength hydrogen peroxide solution are metered in over two hours at an internal temperature of 55-60°. The mixture is further stirred at this temperature for 8 to 10 hours. Then, the mixture is cooled and adjusted to pH=0 with dilute HCl. The reaction solution is heated to 60° C., and the phases are separated while warm. The majority of the n-butyl acetate is removed under reduced pressure. The resulting thick slurry is cooled and admixed with a small amount of toluene. The precipitate is filtered off with suction, washed with water and dried. 8.7 g of 2-methyl-3-(methylsulfonyl)-4-(trifluoromethyl)benzoic acid (81% yield) are obtained as a white solid.

Preparation of the general compounds VIII, example: 2-methyl-1,3-bis(methylsulfonyl)-4-(trifluoromethyl)benzene 0.7 g of 2-methyl-1,3-bis(methylsulfanyl)-4-(trifluoromethyl)benzene (2.77 mmol, 1 equiv) are initially introduced into dichloromethane (50 ml). 5 g of meta-chloroperbenzoic acid (22 mmol, 8 equiv) are added at room temperature and the mixture is stirred for 20 h. The resulting suspension is filtered, and the filtrate is washed with aqueous bicarbonate and aqueous sodium chloride solution. After removing the solvent under reduced pressure, a white solid is obtained which, for the purposes of recrystallization, is heated in 50 ml of isopropanol, then cooled and filtered. Drying gives 0.76 g of 2-methyl-1,3-bis(methylsulfonyl)-4-(trifluoromethyl)benzene (86% yield) as white crystals.

$^1$H-NMR (600 MHz, CD$_3$CN): δ 8.48 (d, 1H, J=8.6 Hz) 8.08 (d, 1H, J=8.6 Hz), 3.35 (s, 3H), 3.26 (s, 3H), 3.11 (s, 3H). LC/MS (ESI-neg): m/e=315.0 (M-1).

The invention claimed is:
1. Process for preparation of 2-alkyl-4-trifluoromethyl-3-alkylsulfonylbenzoic acid of formula (I), wherein
   a) in a first step a 1,3-dichloro-2-alkyl-4-trifluoromethylbenzene (II) is reacted with a thiolate (IV) to give an aryl bisthioether (III),
   b) in a second step the aryl bisthioether (III) is reacted with an oxidizing agent selectively to give an aryl monosulfoxide monothioether (V),
   c) in a third step an exchange of the sulfoxide group for a metal takes place and the organometallic compound thus obtained is converted to the benzoic acid (VII), and
   d) in a fourth step the remaining thio group is oxidized with an oxidizing agent, optionally in the present of an oxidation catalyst:

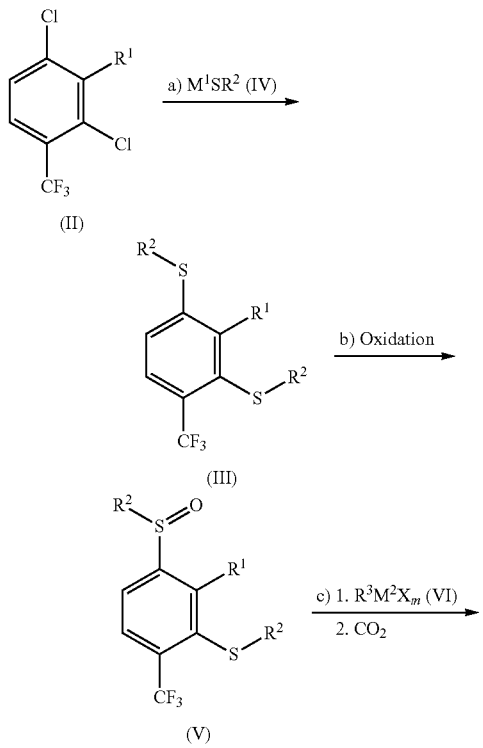

-continued

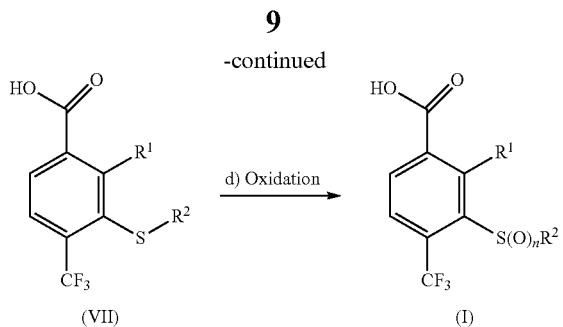

and e) in which the substituents are defined as follows:
   $R^1$ and $R^2$ are, independently of one another, $C_1$-$C_4$-alkyl or phenyl substituted by s radicals from the group consisting of chlorine, fluorine, methoxy and ethoxy,
   $R^3$ is $C_1$-$C_{10}$ alkyl or phenyl substituted by s radicals from the group consisting of chlorine, fluorine, methoxy and ethoxy,
   $M^1$ is lithium, sodium or potassium,
   $M^2$ is magnesium, lithium or zinc,
   X is chloride, bromide or iodide,
   m is 0 or 1,
   n is 1 or 2,
   s is 0, 1, 2 or 3.

2. Process according to claim 1, in which NaSMe or KSMe is used as thiolate (IV).

3. Process according to claim 1, in which the thiolate (IV) is used in a molar ratio of 2:1 to 3:1, based on the compound of formula (II).

4. Process according to claim 1, in which, in the first step, dimethyl sulfoxide, dimethylacetamide, dimethylformamide or N-methyl-2-pyrrolidone is used as solvent.

5. Process according to claim 1, in which, in the second step, $H_2O_2$ is used for selective oxidation.

6. Process according to claim 1, in which, in the second step, acetic acid, propionic acid or dichloromethane is used as solvent.

7. Process according to claim 1, in which $Na_2WO_4$ in an amount of 5 to 15 mol %, and hydrogen peroxide in an amount of 3 to 8 mol equivalents, in each case based on the compound of formula (VII), are used as oxidation catalyst.

8. Process according to claim 1, in which, in the third step, ethylmagnesium bromide, butylmagnesium chloride or isopropylmagnesium chloride is used as organometallic compound.

9. Process according to claim 1, in which, in the third step, toluene, tetrahydrofuran or 2-methyltetrahydrofuran is used as solvent.

10. Compound of formula (III),

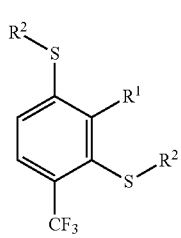

in which
   $R^1$ and $R^2$ are, independently of one another, $C_1$-$C_4$-alkyl or phenyl substituted by s radicals from the group consisting of chlorine, fluorine, methoxy and ethoxy,
   s is 1, 2 or 3.

11. Compound according to claim 10, in which $R^1$ and $R^2$ are methyl, ethyl, n-propyl, isopropyl or n-butyl.

12. Compound of formula (V),

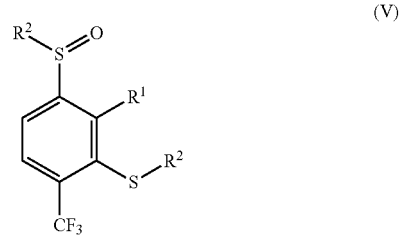

in which
   $R^1$ and $R^2$ are, independently of one another, $C_1$-$C_4$-alkyl or phenyl substituted by s radicals from the group consisting of chlorine, fluorine, methoxy and ethoxy,
   s is 1, 2 or 3.

13. Compound according to claim 12, in which $R^1$ and $R^2$, independently of one another, are methyl, ethyl, n-propyl, isopropyl or n-butyl.

14. Compound of formula (VIII),

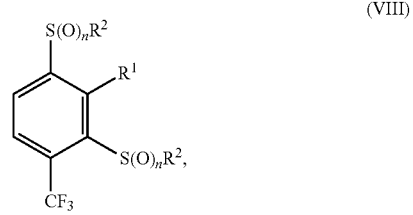

in which
   $R^1$ and $R^2$ are, independently of one another, $C_1$-$C_4$-alkyl or phenyl substituted by s radicals from the group consisting of chlorine, fluorine, methoxy and ethoxy,
   s is 1, 2 or 3,
   n is 1 or 2.

15. Compound according to claim 14, in which $R^1$ and $R^2$, independently of one another, are methyl, ethyl, n-propyl, isopropyl or n-butyl.

* * * * *